(12) United States Patent
Bokrantz et al.

(10) Patent No.: US 11,027,148 B2
(45) Date of Patent: Jun. 8, 2021

(54) SYSTEM AND METHOD FOR PLANNING A RADIATION THERAPY TREATMENT

(71) Applicant: RaySearch Laboratories AB, Stockholm (SE)

(72) Inventors: Rasmus Bokrantz, Stockholm (SE); Albin Fredriksson, Stockholm (SE)

(73) Assignee: RaySearch Laboratories AB, Stockholm (SE)

(*) Notice: Subject to any disclaimer, the term of this patent is extended or adjusted under 35 U.S.C. 154(b) by 35 days.

(21) Appl. No.: 16/481,150

(22) PCT Filed: Jan. 27, 2017

(86) PCT No.: PCT/EP2017/051748
§ 371 (c)(1),
(2) Date: Jul. 26, 2019

(87) PCT Pub. No.: WO2018/137772
PCT Pub. Date: Aug. 2, 2018

(65) Prior Publication Data
US 2019/0358469 A1    Nov. 28, 2019

(51) Int. Cl.
*A61N 5/10*    (2006.01)

(52) U.S. Cl.
CPC ........... *A61N 5/1031* (2013.01); *A61N 5/103* (2013.01); *A61N 5/1042* (2013.01); *A61N 2005/1092* (2013.01)

(58) Field of Classification Search
CPC ..... A61B 5/103; A61B 5/1031; A61B 5/1042; A61B 2005/1092
See application file for complete search history.

(56) References Cited

U.S. PATENT DOCUMENTS

2012/0136194 A1    5/2012    Zhang et al.

FOREIGN PATENT DOCUMENTS

| WO | WO-2016/116868 A1 | 7/2016 | |
| WO | WO-2016/188754 A1 | 12/2016 | |
| WO | WO-2016188754 A1 * | 12/2016 | ........... A61N 5/1048 |

* cited by examiner

*Primary Examiner* — Mark R Gaworecki
(74) *Attorney, Agent, or Firm* — Faegre Drinker Biddle & Reath LLP

(57) ABSTRACT

A system plans a radiation therapy treatment of a target volume based on inputs in the form of: a set of candidate beams (B), where each beam defines an arrangement of a therapeutic beam relative to the target volume; a treatment plan (x) for the radiation therapy treatment that uses a subset of the candidate beams (B); an objective function (F) describing a quality of the treatment plan (x); and a feasible region (X) describing requirements on the treatment plan (x) that must be fulfilled. The objective function (F) and/or the feasible region (X) also reflect a first complexity criterion $(\tau(x) \leq \hat{\tau})$ limiting a first complexity measure $(\tau(x))$ to be less than or equal to a maximum first complexity $(\hat{\tau})$. An optimization step is executed repeatedly; whereby, in each iteration, an updated treatment plan (x') is calculated by optimizing the treatment plan (x) with respect to the objective function (F) and the feasible region (X). Here, if a termination criterion is fulfilled, a set of selected beams (B*) is calculated based on the updated treatment plan (x'). The set of selected beams (B*) is a subset of the set of candidate beams (B). Otherwise, the updated treatment plan (x') is set to the treatment plan (x); an updated first complexity criterion $(\tau'(x) \leq \hat{\tau}')$ is calculated; the updated first complexity criterion $(\tau'(x) \leq \hat{\tau}')$ is set to the first complexity criterion $(\tau(x) \leq \hat{\tau})$, and another iteration of the optimization step is executed.

29 Claims, 3 Drawing Sheets

SYSTEM AND METHOD FOR PLANNING A RADIATION THERAPY TREATMENT

This application is the National Stage of International Application No. PCT/EP2017/051748, filed Jan. 27, 2017, the entire contents of which is incorporated by reference herein.

TECHNICAL FIELD

The present invention relates generally to planning of radiation therapy treatments. More particularly the invention relates to a system for planning a radiation therapy treatment and a corresponding method. The invention also relates to a computer program and a processor-readable medium.

BACKGROUND

In radiation therapy treatment, one or more therapeutic radiation beams are used to deliver a dose to a treatment volume in a patient. Here, the respective orientations of the therapeutic radiation beams are important parameters. The orientation of a therapeutic radiation beam is generally determined by the position of the radiation source, the direction of the beam central axis and the rotation of the treatment head.

In a CyberKnife™ machine, the orientation parameters may be controlled directly via a linear accelerator mounted on a robotic arm. Here, orientations that belong to a single source position are said to belong to a common node.

In a machine with a so-called a C-arm carrying a linear accelerator, where the radiation source rotates around the patient at a constant source-axis distance, a beam orientation is defined by an isocenter position and a triplet of angles describing the rotation of the treatment gantry, the patient couch and the treatment head (the collimator angle) respectively. For C-arm mounted machines it is also common to discriminate between coplanar treatments, where the couch angle is constant for all beams, and general non-coplanar treatments.

The therapeutic beam from a particle therapy machine can be directed upon the patient using a rotating gantry similar to a C-arm mounted linear accelerator.

For delivery techniques where beam orientation is unchanged during irradiation, (e.g. in 3D conformal radiation therapy (3D-CRT), static-field intensity-modulated radiation therapy (IMRT) and intensity-modulated particle therapy (IMPT)), the set of beam orientations corresponds directly to a set treatment beams.

A set of beam orientations can also be translated to a continuous trajectory for arc therapies, where the beam sweeps over the patient during irradiation, such as in volumetric-modulated arc therapy (VMAT).

A discrete set of beam orientations can be converted to a continuous arc trajectory by for example identification of a "shortest path" between the beam orientations, in the sense that the time necessary to move the beam between the set of orientations is minimized. 3D-CRT, IMRT and VMAT are examples of different photon therapy techniques, which are delivered using a C-arm mounted linear accelerator. IMPT may be delivered from a fixed beam line, or by using a rotating gantry.

The general problem of selecting an appropriate subset of beam orientations from a larger candidate set of beam orientations is far from trivial to solve.

Today, a number of different approaches exist to optimize the beam orientations, for example so-called greedy methods that begin with zero beams and then iteratively add one beam at the time. Here, a multitude of optimizations must be performed at each iteration—one for each candidate beam that has not yet been selected—and since the number of candidate beams typically is very large, these computations tend to be highly processing intense. In any case, the selected beam at each iteration is the candidate beam that gives the best improvement in objective function value. Therefore, the greedy methods cannot easily provide a feasible treatment plan within a short calculation time. The calculation times can be reduced by the use of only few optimization iterations per sub-problem, or even by the use gradient information from the first iteration alone. However, such simplifications render the beam selection highly approximate, and thus of relatively low quality.

Mixed-integer programming methods represent another alternative, wherein the beam orientation optimization problem is solved to global optimality by a structured enumeration of all possible solutions. The mixed-integer programming methods are very computationally costly, and are therefore not practicable for realistic problem sizes.

Stochastic search methods represent another example, where beams are randomly swapped and the interchange is kept if it improves the objective function value. This type of approach also tends to be processing intense, or at least time consuming. There are also meta-heuristics, such as simulated annealing and genetic algorithms, which improve on a current set of selected beams using a combination of stochasticity and predefined search rules. The stochastic search methods and the meta-heuristics also require long calculation times in order to be able to sample a large portion of the search space.

One additional option is to employ local search methods that consider the continuous beam angle space and tries to improve the objective function value by using gradients calculated by sensitivity analysis or finite differences. Nevertheless, the local search methods are only useful for fine-tuning because beam orientation optimization problems have many local minima.

Finally, there are geometric methods, which analyze the patient anatomy and that calculate quality scores for the candidate beam directions without performing any treatment plan optimization. The geometric methods can be very fast. However, they have a limited accuracy because they do not rely on actual treatment plan optimization.

In the light of the above problems and shortcomings, the prevailing clinical practice is therefore to select beam orientations manually. Of course, this is far from ideal.

SUMMARY

The object of the present invention is to mitigate the above problems, and offer a therapy planning solution which enables a user-friendly interface and that is efficient with respect to the processing resources required to select a subset of beam orientations to use from a larger candidate set of beam orientations that potentially could be used.

According to one aspect of the invention, the object is achieved by a system for planning a radiation therapy treatment in which a target volume is irradiated by a therapeutic beam. The system includes a processor and a memory. The memory contains instructions executable by the processor whereby the system is operative to execute the following consecutive steps.

Obtaining a set of inputs, including: a set of candidate beams, where each beam in the set of defines an arrangement of the therapeutic beam relative to the target volume; a treatment plan for the radiation therapy treatment that uses a subset of the candidate beams; an objective function describing a quality of the treatment plan; and a feasible region describing requirements on the treatment plan that must be fulfilled, the objective function and/or the feasible region reflecting a first complexity criterion limiting a first complexity measure to be less than or equal to a maximum first complexity. The first complexity measure is related to a delivery time for the treatment plan;

Executing an optimization step whereby an updated treatment plan is calculated by optimizing the treatment plan with respect to the objective function and the feasible region; and Checking if a termination criterion is fulfilled. If so, a set of selected beams is calculated based on the updated treatment plan, where the set of selected beams is a subset of the set of candidate beams. Otherwise, the updated treatment plan is set to the treatment plan; an updated first complexity criterion is calculated; the updated first complexity criterion is set to the first complexity criterion; and the procedure returns to the optimization step for another iteration.

This system is advantageous because the proposed strategy of gradually eliminating beams from the treatment plan leads to a calculation process that becomes less computing-intensive for each iteration. Moreover, already the initial steps require relatively low computing power. Thus, the overall planning process can be made highly efficient in terms of time and computation efforts.

According to one embodiment of this aspect of the invention, the system further contains at least one input interface and an output interface. The at least one input interface is configured to receive definitions of the objective function and the feasible region, for example via manual user inputs, a local data store or from an online resource. The output interface is configured to output the determined set of selected beams, e.g. for presentation on a display or storage, locally and/or remotely. These interfaces are advantageous because they provide a high degree of flexibility in terms of origin of the source data and destination for the result data.

According to another embodiment of this aspect of the invention, the first complexity criterion represents a continuous and differentiable approximation of a second complexity criterion. Namely, the second complexity criterion limits a second complexity measure within a maximum second complexity, and the second complexity measure is indicative of a number of beams in the set of candidate beams that is used in the treatment plan. However, the second complexity criterion, as such, is typically a so-called step function, which is not differentiable everywhere. Consequently, the proposed first complexity criterion (that is based on said continuous and differentiable approximation) facilitates the optimization computations substantially. Moreover, the instructions executable by the processor render the system further operative to, prior to returning to the optimization step, calculate an updated second complexity criterion and setting the updated second complexity criterion to the second complexity criterion. This means that, analogous to the first complexity criterion, the second complexity criterion is also updated before the optimization continues.

According to yet another embodiment of this aspect of the invention, the set of inputs further contains a final maximum first complexity. The instructions executable by the processor also render the system operative to calculate the updated first complexity criterion such that, prior to returning to a final iteration of the optimization step. The maximum first complexity is equal to the final maximum first complexity. Thereby, the complexity of the resulting treatment plan can be known in advance.

According to still another embodiment of this aspect of the invention, analogous to the above, the set of inputs contains a final maximum second complexity, and the instructions executable by the processor render the system further operative to calculate the updated second complexity criterion such that, prior to returning to a final iteration of the optimization step, the maximum second complexity is equal to the final maximum second complexity.

According to a further embodiment of this aspect of the invention, the termination criterion is based on one or more of the following: [a] a maximum number of iterations of the optimization step, [b] the first complexity measure is less than or equal to the final maximum first complexity, [c] the second complexity measure is less than or equal to the final maximum second complexity, and [d] a user input is received, which user input designates a stop command. Hence, a high degree flexibility is attained with respect to the conditions for ending the optimization process.

According to another embodiment of this aspect of the invention, the instructions executable by the processor render the system further operative to, prior to returning to the optimization step, execute an updating process containing the following steps. Calculating an updated set of candidate beams based on the updated treatment plan, where the updated set of candidate beams is a subset of the set of candidate beams; setting the updated set of candidate beams to the set of candidate beams; calculating an updated feasible region reflecting the requirements of the feasible region and a requirement that only beams in the set of candidate beams can be used in the treatment plan; and setting the updated feasible region to the feasible region. This means that the treatment plans is based exclusively on beams that actually contribute to the irradiation of the treatment volume.

According to an additional embodiment of this aspect of the invention, the instructions executable by the processor render the system further operative to, following the above updating process and prior to returning to the optimization step, calculate a further updated treatment plan based on the updated treatment plan and the feasible region. The feasible region here contains the further updated treatment plan. Hence, the optimization can continue based on the further updated treatment plan.

According to another embodiment of this aspect of the invention, the instructions executable by the processor render the system further operative to, following the updating process and prior to returning to the optimization step, either (a) set the updated treatment plan to the treatment plan, or (b) set the further updated treatment plan to the treatment plan depending on which version of the treatment plan that currently is available.

According to still another embodiment of this aspect of the invention, prior to returning to the optimization step, the updated set of candidate beams is calculated such that: a first complexity measure of the further updated treatment plan is less than or equal to the maximum first complexity, and/or a second complexity measure of the further updated treatment plan is less than or equal to the maximum second complexity. This keeps the degree of complexity moderate throughout the optimization process.

According to an additional embodiment of this aspect of the invention, the updated set of candidate beams is calculated such that an objective function value for the further updated treatment plan is as close as possible to an objective function value for the updated treatment plan. Alternatively the updated set of candidate beams is calculated by excluding at least one beam from the set of candidate beams. The excluded beam(s) is(are) the one(s) that contribute(s) the least to the updated treatment plan. In both cases, speedy convergence can be expected.

According to another embodiment of this aspect of the invention, the objective function and/or the feasible region describes a quality of a plan for the radiation therapy treatment in terms of a deviation of a planned dose from a desired radiation dose. The planned dose is here calculated on the basis of image data defining the target volume, for example received by the system via the input interface. Thereby, conventional CT scan or MRI data can be used for the therapy planning.

According other embodiments of this aspect of the invention, the initial treatment plan obtained in the set of inputs represents one of the following three alternatives.

According to a first alternative, the treatment plan involves irradiating the target volume using a subset of the beams in the set of candidate beams. The therapeutic beam for each beam in the subset of the set of candidate beams is conformed to the target volume and has a uniform fluence profile. Further, the fluence profile for the therapeutic beam for each beam in the subset of the set of candidate beams is scaled such that an average planned dose for the target volume is equal to a prescribed target dose.

According to a second alternative, the treatment plan involves delivering no irradiation at all; and according to a third alternative, the treatment plan involves delivering irradiation using a subset of the beams in the set of candidate beams according to a previously generated treatment plan.

According to still another embodiment of this aspect of the invention, the set of candidate beams is a discretization of a continuous set of possible arrangements of the therapeutic beam. The continuous set of possible arrangements, in turn, is based on: a plurality of mechanical capabilities of a therapy machine, a positioning of a patient relative to a therapy machine, and/or a specification of desirable arrangements. Hence, adequate parameters of the therapy and the machine to be used can be weighted in into the optimization process.

According to another aspect of the invention, the object is achieved by a method of planning a radiation therapy treatment in which a target volume is irradiated by a therapeutic beam. The method contains the following consecutive steps.

Obtaining a set of inputs in a processor, where the set of inputs includes: a set of candidate beams, where each beam defines an arrangement of the therapeutic beam relative to the target volume; a treatment plan for the radiation therapy treatment that uses a subset of the candidate beams; an objective function describing a quality of the treatment plan; and a feasible region describing requirements on the treatment plan that must be fulfilled. The objective function and/or the feasible region reflects a first complexity criterion limiting a first complexity measure to be less than or equal to a maximum first complexity. The first complexity measure, in turn, is related to a delivery time for the treatment plan. In other words, a relatively low first complexity measure corresponds to a treatment plan associated with a comparatively short delivery time, and vice versa;

Executing an optimization step, whereby an updated treatment plan is calculated by optimizing the treatment plan with respect to the objective function and the feasible region; and Checking if a termination criterion is fulfilled. If so, a set of selected beams is calculated based on the updated treatment plan, where the set of selected beams is a subset of the set of candidate beams. Otherwise (i.e. if the termination criterion is not fulfilled), the updated treatment plan is set to the treatment plan; an updated first complexity criterion is calculated; the updated first complexity criterion is set to the first complexity criterion; and the procedure returns to the above optimization step.

The advantages of this method, as well as the preferred embodiments thereof, are apparent from the discussion above with reference to the proposed system.

According to a further aspect of the invention the object is achieved by a computer program loadable into the memory of at least one processor, and includes software adapted to implement the method proposed above when said program is run on at least one processor.

According to another aspect of the invention the object is achieved by a processor-readable medium, having a program recorded thereon, where the program is to control at least one processor to perform the method proposed above when the program is loaded into the at least one processor.

One general advantage of the invention compared to the known solutions is that all the potentially available beam orientations in the machine are considered in at least some stage of the algorithm. The invention also enables easy control of the calculation time.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

DETAILED DESCRIPTION

The invention aims at selecting a subset of suitable beam orientations to use from a larger candidate set of beam orientations that are potentially usable in order to provide a prescribed therapy of a treatment volume.

To achieve this goal, it is necessary to satisfy the standard requirements for treatment plan optimization. Therefore, a set of parameters describing the treatment has been selected as optimization variables. Moreover, a feasible set of these variables has been defined, and an objective function that quantifies treatment plan quality has been formulated. Examples of variables for photon techniques such as 3D-CRT, static-field IMRT and VMAT are the energy fluence per bixel (a surface element in the beam planes), multileaf collimator leaf positions, dose rates and delivery times per segment, or beam weights. Standard variables for IMPT are scanning times per spot. The set of feasible variables is defined by constraints that reflect the physical limitations of the delivery method, and can also include constraints on the planned dose distribution. An objective function for treatment planning generally penalizes deviations between the planned dose and the desired dose. However, the objective function may also take other aspects of the treatment plan into account, such as the geometric complexity of the optimized collimator shapes. The treatment planner generally makes a choice about which requirements on the dose and the variables that are posed as part of the objective function (requirements for which errors are minimized), and which requirements that are posed as constraints in the formulation of the feasible region (requirements that must be satisfied completely). Nevertheless, the exact choice of variables, feasible region and objective functions is irrelevant for the solution according to the invention.

It is also necessary that a finite set of candidate beam orientations is defined. Such a set can either be generated in a fully automated fashion, or be created based on inputs from the treatment planner. Possible parameters that may be used to define the finite set of candidate beam orientations are whether non-coplanar beam orientations should be allowed, whether variable collimator angles should be allowed and the level of discretization for the set of possible gantry, couch and collimator angles. Naturally, combinations of angles which would cause a collision between the patient and the treatment head should be removed from the candidate set. The same is true for angles within a set of forbidden angles assigned by the treatment planner for other reasons.

Figure 1:
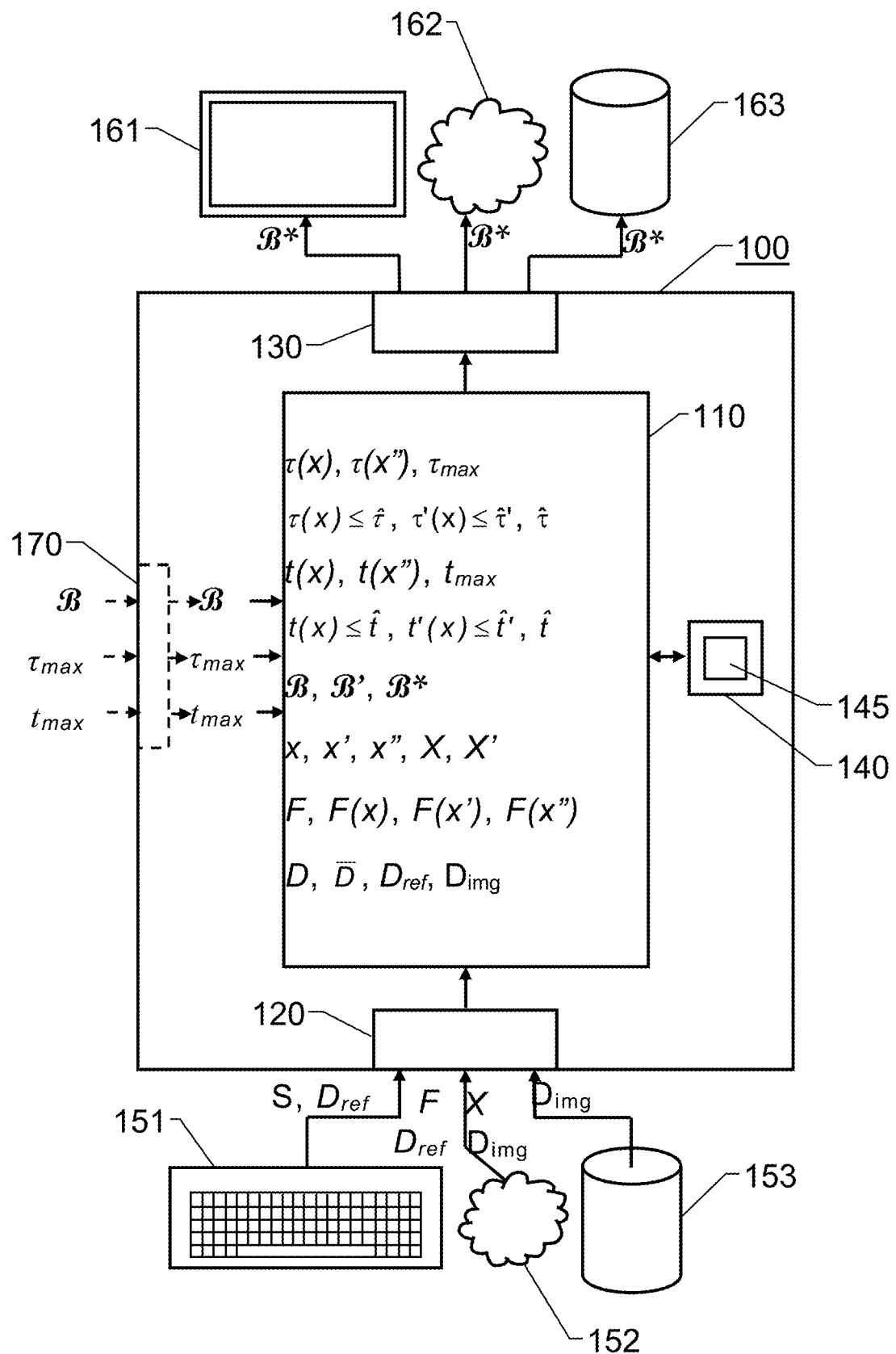
FIG. 1 shows an overview of a therapy planning system according to one embodiment of the invention.

FIG. 1 shows an overview of a system 100 according to one embodiment of the invention for planning a radiation therapy treatment in which a target volume is irradiated by a therapeutic beam. The system 100 includes a processor 110 and a memory 140. The memory 140, in turn, contains instructions 145 (i.e. software) executable by the processor 110, whereby the system 100 is operative to execute the consecutive steps [$S_{11}$], [$S_{12}$] and [$S_{13}$] in a possibly repeated manner. However, before describing steps [$S_{11}$], [$S_{12}$] and [$S_{13}$], we will explain the rationale behind the proposed procedure by describing the beam optimization mathematically.

Let $\mathcal{B}$ be the number of elements in $\mathcal{B}$.

Further, let $x=(x_1, \ldots, x_{|\mathcal{B}|})^T$ be a vector of optimization variables, which is composed of sub-vectors $x_b$ that define the optimization variables related to a given beam orientation b in $\mathcal{B}$.

X is the set of feasible variable vectors (i.e. the abovementioned feasible region).

F is the objective function that takes x to a measure of plan quality, with lower values being preferred.

$y=(y_1, \ldots, y_{|\mathcal{B}|})^T$ is a function with components $y_b$ measuring the contribution of $x_b$ to the overall treatment, which is defined such that: $y_b(x_b)=0$ if $x_b$ has values corresponding to b not being used for treatment, and $y_b(x_b)>0$ otherwise.

t is a function that takes y(x) to a measure of a plan complexity, where t is defined such that it depends on the cardinality of y(x) (i.e. the number of nonzero elements of this vector), denoted card(y(x)). Below, we will elaborate upon proposed first and second complexity measures τ(x) and t(x) respectively for quantifying the plan complexity.

Examples of possible measures $y_b$ are the integral dose to the target volume delivered from beam b, the beam-on time for beam b, or some norm of the vector $x_b$. The function t may for example be the cardinality of y, or the cardinality of y plus some norm of y.

The first example corresponds to the case where a number of static beams should be controlled, and the second example to the case where the total treatment time should be controlled, with the cardinality term representing a constant time-cost for an additional static beam and the norm term representing the beam-on time for such a beam. A possible definition of t for arc therapy is the length of the shortest feasible path that connects the subset of beam orientations {$b \in \mathcal{B} : y_b(x_b)>0$} that are used for treatment (or some approximation of such a path length). A definition of t for CyberKnife™ treatments is a vector where the first component measures the cardinality of the number of nodes that are used for treatment and the second component measures the cardinality of the number of beam orientations being used for treatment.

The beam orientation optimization can now be stated as the problem:

$$\underset{x}{\text{minimize}}\; F(x) \text{ subject to } x \in X,\, t(x) \leq t_{max} \qquad (P1)$$

where t is bounded within some maximum acceptable complexity $t_{max}$, or $$\underset{x}{\text{minimize}}\; F(x) + G(t(x)) \text{ subject to } x \in X \qquad (P2)$$

with G being a penalty on t(x), for example $$G(t(x))=\lambda(\max\{t(x)-t_{max}, 0\} \text{ for a positive weight } \lambda.$$

A solution x* to (P1) or (P2) defines a set of selected beam orientations $\mathcal{B}^*$, where $\mathcal{B}^*=\{b \in \mathcal{B} : y_b(x^*_b)>0\}$.

However, the optimization problems (P1) and (P2) are very difficult to solve because the cardinality of y must be controlled during optimization. Such general convex-cardinality problems are known to be non-deterministic polynomial-time hard (NP-hard).

Therefore, according to the invention, a heuristic is used to instead find an approximate solution to the problem (P1) or (P2) within a practical calculation time. The heuristic approximates t by a continuous and differentiable function r, which is better suited for optimization. Here, the subscript E indicates a parameter that controls the accuracy of the approximation.

The heuristic also successively removes beams from the set of candidate beams $\mathcal{B}$ to a subset of selected beams $\mathcal{B}^*$. More precisely, the set of candidate beams $\mathcal{B}$ is updated by defining $\mathcal{B}$ as a subset of selected beams in $\mathcal{B}$, and then replacing the previous set of candidate beams $\mathcal{B}$ with the subset of selected beams $\mathcal{B}^*$.

The beam orientations thus removed are the ones, which are constrained to give a zero contribution to the treatment, or at least give an insufficient contribution.

Together, this provides an approximate counterpart of (P1) in the form of:

$$\underset{x}{\text{minimize}}\; F(x) \text{ subject to } x \in X,\, \tau_\varepsilon(x) \leq \bar{\tau},\, y_b(x_b) = 0,\, b \notin \bar{\mathcal{B}} \qquad (A1)$$

where $\hat{\tau}$ is a complexity limit,
and an approximate counterpart of (P2) in the form of:

$$\underset{x}{\text{minimize}}\ F(x) + G(\tau_\varepsilon(x))\ \text{subject to}\ x \in X,\ y_b(x_b) = 0,\ b \notin \mathcal{B}. \quad \text{(A2)}$$

It is possible to obtain a continuous approximation of the cardinality of an n-vector z by utilizing the fact that card(z) can be ex-pressed as a sum of step functions s according to:

$$\text{card}(z) = \sum_{i=1}^{n} s(z_i)\ \text{where}\ s(z_i) = \begin{cases} 0 & \text{if}\ z_i \leq 0 \\ 1 & \text{otherwise} \end{cases}$$

and the fact that the step function s can be approximated by a continuous function. Here, it should be noted that n=|$\mathcal{B}$| when card (•) is applied to y.

Figure 2A:
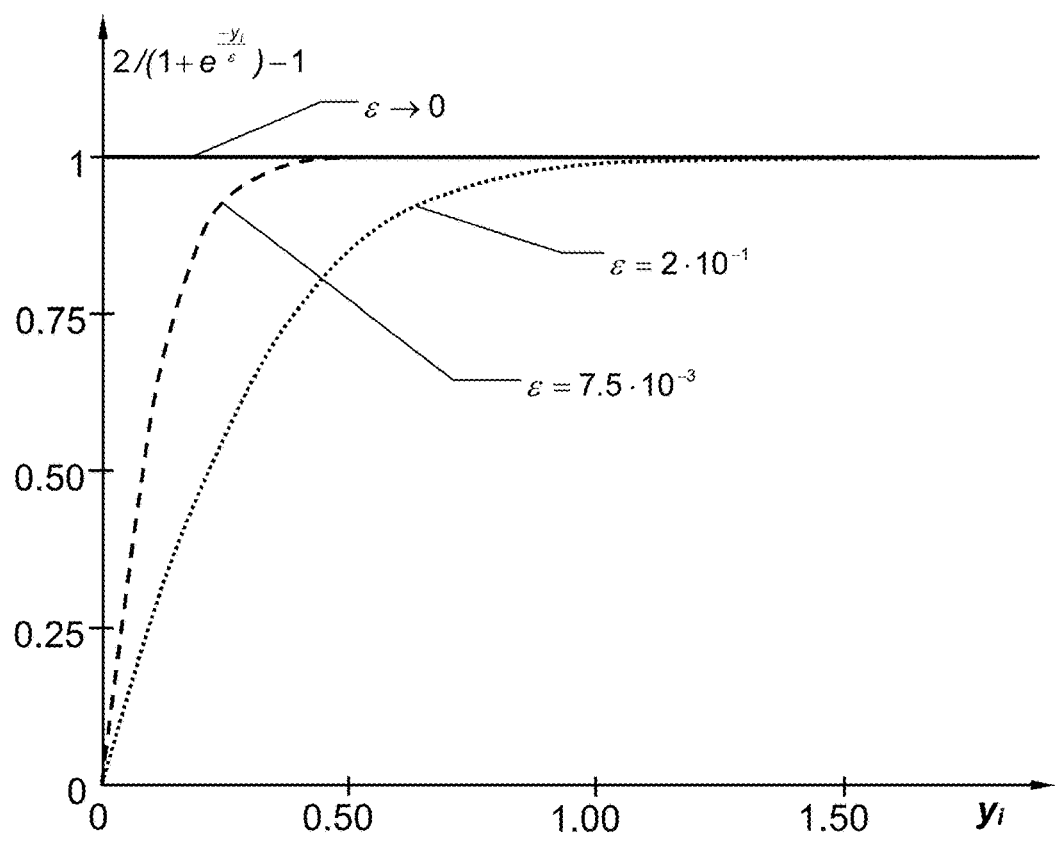
FIGS. 2a-b exemplifies first complexity measures representing continuous and differentiable functions that approximate a step function representing a second complexity measure according to one embodiment of the invention.
Figure 2B:
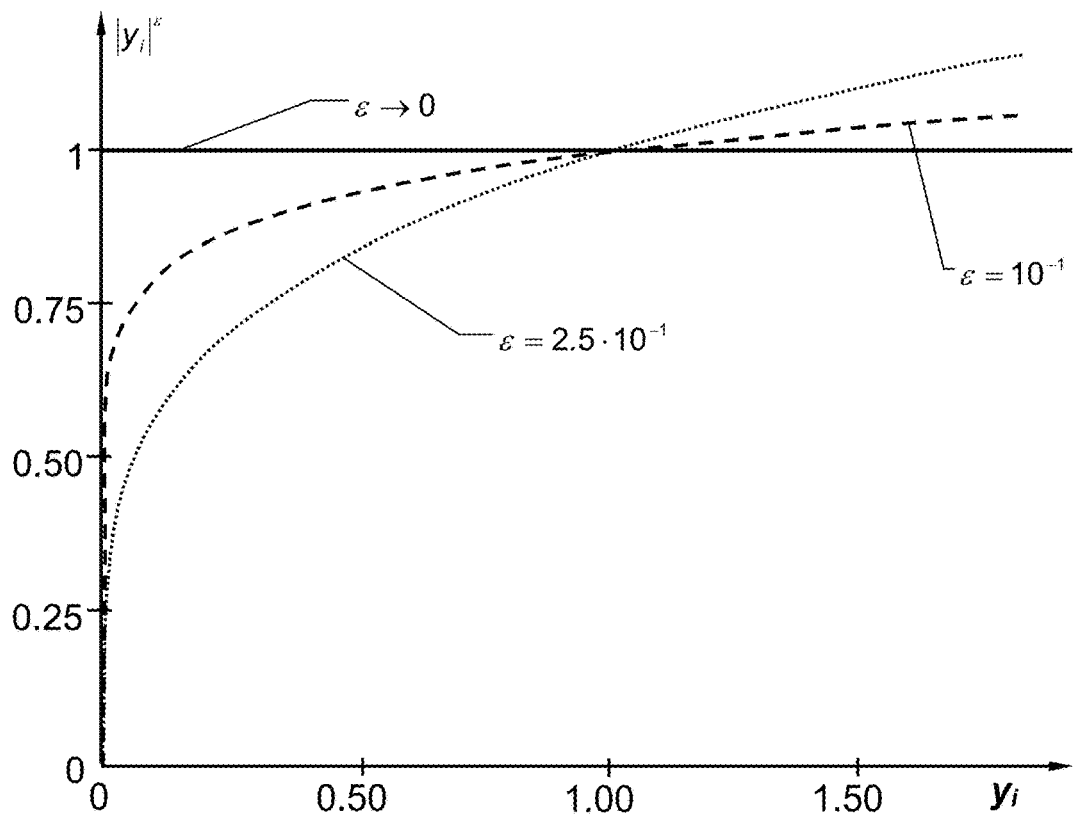

FIGS. 2a and 2b show first and second examples of continuous approximations of card(y) that are smooth in the positive domain.

More precisely, FIG. 2a represents a sum of logistic functions according to:

$$\sum_{i=1}^{n}\left(\frac{2}{1+e^{-y_i/\varepsilon}} - 1\right),$$

and

FIG. 2b represents an ε-norm of y according to:

$$\sum_{i=1}^{n}|y_i|^\varepsilon.$$

Both these approximations approach card(y) as ε approaches zero as can be seen in FIGS. 2a and 2b showing the inner summands in (A1) and (A2) respectively.

Moreover, the optimization problems in (A1) and (A2) are continuous optimization problems for which many general purpose solvers are applicable.

As will be described below, examples of termination criteria for the optimization are that the current iterate x has converged in some sense, or that some form of timeout has occurred, e.g., a maximum number of iterations has been reached. The initial point for the optimization can either be a preselected initial guess (e.g. uniform fluence profiles scales such that the target dose is equal to the prescription dose on average)

In the light of the above, the following procedure is applied according to the invention. Specifically, the instructions 145 in the memory 140 being executable by the processor 110 render the system 100 operative to execute the consecutive steps [$S_{11}$], [$S_{12}$] and [$S_{13}$].

In step [$S_{11}$], a set of inputs is obtained, either from an internal storage in the system 100 or via one or more interfaces 120.

The set of inputs contains a set of candidate beams $\mathcal{B}$, where each beam in the set of candidate beams $\mathcal{B}$ defines an arrangement of the therapeutic beam relative to the target volume. The set of inputs also contains a treatment plan x for the radiation therapy treatment that uses a subset of the candidate beams $\mathcal{B}$. Further, the set of inputs contains an objective function F describing a quality of the treatment plan x, and a feasible region X describing requirements on the treatment plan x that must be fulfilled.

The treatment plan x, obtained in the set of inputs, may represent irradiating the target volume using a subset of the beams in the set of candidate beams $\mathcal{B}$. The therapeutic beam for each beam in the subset of the set of candidate beams $\mathcal{B}$ is conformed to the target volume and has a uniform fluence profile. The fluence profile for the therapeutic beam for each beam in the subset of the set of candidate beams $\mathcal{B}$ is further scaled such that an average planned dose $\overline{D}$ for the target volume is equal to a prescribed target dose.

Alternatively, the treatment plan x, obtained in the set of inputs, may represent delivering no irradiation; or delivering irradiation using a subset of the beams in the set of candidate beams 9 according to a previously generated treatment plan.

The objective function F and/or the feasible region X reflects a first complexity criterion $\tau(x) \leq \hat{\tau}$, which limits a first complexity measure $\tau(x)$ to be less than or equal to a maximum first complexity $\hat{\tau}$. The first complexity measure $\tau(x)$ is related to a delivery time for the treatment plan x. This means that a relatively low first complexity measure corresponds to a treatment plan that is associated with a comparatively short delivery time, and vice versa.

The objective function F and/or the feasible region X preferably also describes a quality of a plan for the radiation therapy treatment in terms of a deviation of a planned dose D from a desired radiation dose $D_{ref}$. The planned dose D, in turn, is calculated based on of image data $D_{img}$ defining the target volume. The image data $D_{img}$ may for example represent CT scan data or MRI data.

To reduce the amount of computations, the set of candidate beams $\mathcal{B}$ is preferably a discretization of a continuous set of possible arrangements of the therapeutic beam. The continuous set of possible arrangements, in turn, may be based on: a plurality of mechanical capabilities of a therapy machine, a positioning of a patient relative to a therapy machine, and/or a specification of desirable arrangements.

In step [$S_{12}$], subsequent to step [$S_{11}$], an optimization step is executed, whereby the processor 110 calculates an updated treatment plan x' by optimizing the treatment plan x with respect to the objective function F and the feasible region X. Thereafter a step [$S_{13}$] is performed.

In step [$S_{13}$] it is checked if a termination criterion is fulfilled; and if so, a set of selected beams $\mathcal{B}$ * is calculated in a step [$S_{131}$]. The set of selected beams $\mathcal{B}$ * is calculated based on the updated treatment plan x'. The set of selected beams $\mathcal{B}$ * is a subset of the set of candidate beams $\mathcal{B}$. I.e. the set of selected beams $\mathcal{B}$ * contains fewer, or at most as many beams as the set of candidate beams $\mathcal{B}$.

If, in step [$S_{13}$], it is found that the termination criterion is not fulfilled, a step [$S_{132}$] follows in which the updated treatment plan x' is set to the treatment plan x. In step [$S_{132}$] an updated first complexity criterion $\tau'(x) \leq \hat{\tau}'$ is also calculated, and the updated first complexity criterion $\tau'(x) \leq \hat{\tau}'$ is set to the first complexity criterion $\tau(x) \leq \hat{\tau}$. Thereafter, the procedure returns to step [$S_{12}$] for further optimization.

Preferably, the system 100 further includes at least one input interface 120 and an output interface 130. The at least one input interface 120 is configured to receive definitions of the objective function F and the feasible region X, for example from a local data store 153, or from an online resource 152. Of course, the definitions the objective function F and the feasible region X may also be entered via manual user inputs through a keyboard 151, a touch screen, or similar input members. In addition, the at least one input interface 120 may receive a description of the desired radiation dose $D_{ref}$ for example via the keyboard 151 or the online resource 152 and/or the image data $D_{img}$ defining the target volume, for example from the online resource 152 or the local data store 153. The output interface 130 is configured to output the determined set of selected beams $\mathcal{B}$, e.g. for presentation on a display 161, for storage in a local data store 163 and/or a remote data resource 162.

As explained above, the first complexity criterion $\tau(x) \leq \hat{\tau}$ preferably represents a continuous and differentiable approximation of a second complexity criterion $t(x) \leq \hat{t}$. Namely, such a continuous and differentiable approximation simplifies the computations in connection with the optimization substantially in relation to corresponding calculations being made on the basic NP-hard problem. Analogous to the first complexity criterion $\tau(x) \leq \hat{\tau}$, the second complexity criterion $t(x) \leq \hat{t}$ limits a second complexity measure $t(x)$ within a maximum second complexity $\hat{t}$. The second complexity measure $t(x)$ is here indicative of a number of beams in the set of candidate beams $\mathcal{B}$ that is used in the treatment plan x.

To gradually improve the treatment plan, the instructions 145 executable by the processor 110 render the system 100 further operative to, prior to returning to step $[S_{12}]$, calculate an updated second complexity criterion $t'(x) \leq \hat{t}'$, and set the updated second complexity criterion $t'(x) \leq \hat{t}'$ to the second complexity criterion $t(x) \leq \hat{t}$.

To ensure reasonable convergence of the optimization, the set of inputs preferably further contains a final maximum first complexity $\tau_{max}$, and the instructions 145 executable by the processor 110 render the system 100 further operative to calculate the updated first complexity criterion $\tau'(x) \leq \hat{\tau}'$ such that, prior to returning to a final iteration of step $[S_{12}]$, the maximum first complexity $\hat{\tau}$ is equal to the final maximum first complexity max.

Alternatively, the set of inputs comprises the final maximum first complexity $\tau_{max}$, however the instructions 145 executable by the processor 110 render the system 100 operative to instead calculate the updated second complexity criterion $t'(x) \leq \hat{t}'$ such that, prior to returning to the final iteration of step $[S_{12}]$, the maximum second complexity $\hat{t}$ is equal to the final maximum second complexity $t_{max}$.

According to one embodiment of the invention, the termination criterion is based on: a maximum number of iterations of step $[S_{12}]$, the first complexity measure $\tau(x)$ being less than or equal to the final maximum first complexity $\tau_{max}$, the second complexity measure $t(x)$ being less than or equal to the final maximum second complexity $t_{max}$ and/or a user input S is received, which user input S designates a stop command. Thereby, the optimization process may be ended when a predetermined criterion is met, as well as at an arbitrary point in time selected by an operator, for example the treatment planner.

Preferably, the instructions 145 executable by the processor 110 render the system 100 further operative to, prior to returning to step $[S_{12}]$, execute an updating process. The updating process, in turn, involves the following steps.

Calculating an updated set of candidate beams $\mathcal{B}'$ based on the updated treatment plan x'. The updated set of candidate beams $\mathcal{B}'$ is here a subset of the set of candidate beams $\mathcal{B}$.

The updated set of candidate beams $\mathcal{B}'$ is then to the set of candidate beams $\mathcal{B}$, and an updated feasible region X' is calculated, which updated feasible region X' reflecting the requirements of the feasible region X and a requirement that only beams in the set of candidate beams $\mathcal{B}$ can be used in the treatment plan x. Thereafter, the updated feasible region X' is set to the feasible region X, and the procedure may loop back to step $[S_{12}]$ for further optimization.

Nevertheless, following the above updating process and prior to returning to step $[S_{12}]$, the processor 110 preferably also calculates a further updated treatment plan x" based on the updated treatment plan x' and the feasible region X. Here, the feasible region X contains the further updated treatment plan x".

Further preferably, the updated set of candidate beams $\mathcal{B}'$ is calculated such that an objective function value F(x") for the further updated treatment plan x" is as close as possible to an objective function value F(x') for the updated treatment plan x'. Namely, this speeds up the convergence of the optimization.

In addition thereto, it is advantageous if calculating the updated set of candidate beams $\mathcal{B}'$ involves excluding at least one beam from the set of candidate beams $\mathcal{B}$, and the at least one beam being thus excluded is the at least one beam that contribute(s) the least to the updated treatment plan x'.

Moreover, following the above updating process and prior to returning to step $[S_{12}]$, the processor 110 preferably executes the steps of setting the updated treatment plan x' to the treatment plan x; or setting the further updated treatment plan x" to the treatment plan x. Thereby, the quality improves of the treatment plan resulting from a final iteration of the optimization step.

According to one embodiment of the invention, the updated set of candidate beams $\mathcal{B}'$ is calculated such that one or both the following conditions are satisfied prior to returning to step $[S_{12}]$.

[i] a first complexity measure $\tau(x")$ of the further updated treatment plan x" is less than or equal to the maximum first complexity $\hat{\tau}$; and

[ii] a second complexity measure $t(x")$ of the further updated treatment plan x" is less than or equal to the maximum second complexity $\hat{t}$.

Figure 3:
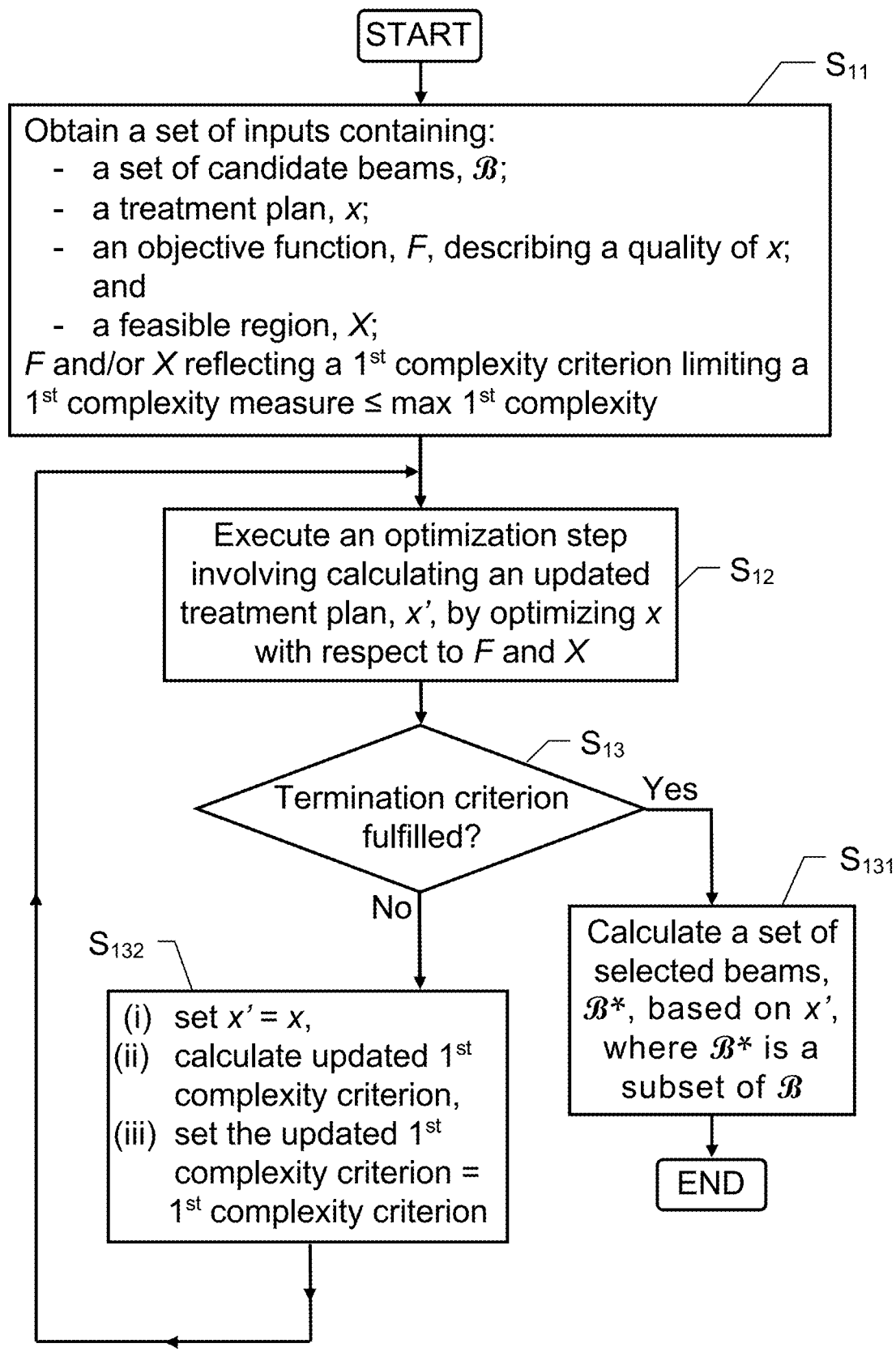
FIG. 3 illustrates, by means of a flow diagram, the general method according to the invention.

In order to sum up, and with reference to the flow diagram in FIG. 3, we will now describe the general method according to the invention for planning a radiation therapy treatment in which a target volume is irradiated by a therapeutic beam.

In a first step $S_{11}$, a set of inputs is obtained in the processor 110. The set of inputs contains a set of candidate beams, $\mathcal{B}$, where each beam defines an arrangement of the therapeutic beam relative to the target volume. The set of inputs also contains a treatment plan x for the radiation therapy treatment, which treatment plan x at uses a subset of the candidate beams $\mathcal{B}$. Moreover, the set of inputs contains an objective function F describing a quality of the treatment plan x and a feasible region X describing requirements on the treatment plan x that must be fulfilled. The objective function F and/or the feasible region X reflects a first complexity criterion $\tau(x) \leq \hat{\tau}$, which limits a first complexity measure $\tau(x)$ to be less than or equal to a maximum first complexity $\hat{\tau}$. The first complexity measure $\tau(x)$ is related to a delivery time for the treatment plan x.

Then, in a step $S_{12}$ an optimization step is executed, whereby an updated treatment plan x' is calculated by optimizing the treatment plan x with respect to the objective function F and the feasible region X.

Thereafter, a step $S_{13}$ checks if a termination criterion is fulfilled; and if so, a step $S_{131}$ follows. Otherwise, the procedure continues to a step $S_{132}$, in which the updated treatment plan x' is set to the treatment plan x. In step $S_{131}$, an updated first complexity criterion $\tau'(x) \leq \hat{\tau}'$ is also calculated, and the updated first complexity criterion $\tau'(x) \leq \hat{\tau}'$ is set to the first complexity criterion $\tau(x) \leq \hat{\tau}$. Subsequently, the procedure loops back to step $S_{12}$ for further optimization.

In step $S_{131}$, a set of selected beams $\mathcal{B}*$ is calculated based on the updated treatment plan x'. The set of selected beams $\mathcal{B}*$ is a subset of the set of candidate beams $\mathcal{B}$. Subsequently, the procedure ends, and a radiation therapy treatment can be presented to a treatment planner, which treatment is based on the set of selected beams $\mathcal{B}*$ and the updated treatment plan x'.

All of the process steps, as well as any sub-sequence of steps, described with reference to FIG. 3 may be controlled by means of a programmed processor. Moreover, although the embodiments of the invention described above with reference to the drawings comprise processor and processes performed in at least one processor, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A system for planning a radiation therapy treatment in which a target volume is irradiated by a therapeutic beam, the system comprising:
    a processor, and
    a memory containing instructions executable by the processor whereby the system is operative to execute the consecutive steps of:
    [$S_{11}$] obtaining a set of inputs, comprising:
        a set of candidate beams (B), each beam in the set of candidate beams (B) defining an arrangement of the therapeutic beam relative to the target volume;
        a treatment plan (x) for the radiation therapy treatment that uses a subset of the candidate beams (B);
        an objective function (F) describing a quality of the treatment plan (x); and
        a feasible region (X) describing requirements on the treatment plan (x) that must be fulfilled,
        at least one of the objective function (F) and the feasible region (X) reflecting a first complexity criterion ($\tau(x) \leq \hat{\tau}$), the first complexity criterion ($\tau(x) \leq \hat{\tau}$) limiting a first complexity measure ($\tau(x)$) to be less than or equal to a maximum first complexity ($\hat{\tau}$), the first complexity measure ($\tau(x)$) being related to a delivery time for the treatment plan (x);
    [$S_{12}$] executing an optimization step whereby an updated treatment plan (x') is calculated by optimizing the treatment plan (x) with respect to the objective function (F) and the feasible region (X);
    [$S_{13}$] checking if a termination criterion is fulfilled;
        and if so, [$S_{131}$] calculating a set of selected beams (B*) based on the updated treatment plan (x'), the set of selected beams (B*) being a subset of the set of candidate beams (B);
        and otherwise, [$S_{132}$] setting the updated treatment plan (x') to the treatment plan (x); calculating an updated first complexity criterion ($\tau'(x) \leq \hat{\tau}'$); setting the updated first complexity criterion ($\tau'(x) \leq \hat{\tau}'$) to the first complexity criterion ($\tau(x) \leq \hat{\tau}$); and returning to step [$S_{12}$],
        wherein the first complexity criterion ($\tau(x) \leq \hat{\tau}$) represents a continuous and differentiable approximation of a second complexity criterion ($t(x) \leq \hat{t}$), the second complexity criterion ($t(x) \leq \hat{t}$) limiting a second complexity measure ($t(x)$) within a maximum second complexity ($\hat{t}$), the second complexity measure ($t(x)$) being indicative of a number of beams in the set of candidate beams (B) that is used in the treatment plan (x);
    prior to returning to step [$S_{12}$], calculating an updated second complexity criterion ($t'(x) \leq \hat{t}'$); and
    setting the updated second complexity criterion ($t'(x) \leq \hat{t}'$) to the second complexity criterion ($t(x) \leq \hat{t}$).

2. The system according to claim 1, wherein the system further comprises:
    at least one input interface configured to receive definitions of the objective function (F) and the feasible region (X), and
    an output interface configured to output the determined set of selected beams (B*).

3. The system according to claim 1, wherein the set of inputs further comprises a final maximum second complexity ($\tau_{max}$), and the instructions executable by the processor render the system further operative to calculate the updated first complexity criterion ($\tau'(x) \leq \hat{\tau}'$) such that, prior to returning to a final iteration of step [$S_{12}$], the maximum first complexity ($\hat{\tau}$) is equal to the final maximum first complexity ($\tau_{max}$).

4. The system according to claim 1, wherein the set of inputs further comprises a final maximum second complexity ($t_{max}$), and the instructions executable by the processor render the system further operative to calculate the updated second complexity criterion ($t'(x) \leq \hat{t}'$) such that, prior to returning to a final iteration of step [$S_{12}$], the maximum second complexity ($\hat{t}$) is equal to the final maximum second complexity ($t_{max}$).

5. The system according to claim 4, wherein the termination criterion is based on at least one of:
    [a] a maximum number of iterations of step [$S_{12}$],
    [b] the first complexity measure ($\tau(x)$) is less than or equal to the final maximum first complexity ($\tau_{max}$),

[c] the second complexity measure (t(x)) is less than or equal to the final maximum second complexity ($t_{max}$), and

[d] a user input (S) is received, which user input (S) designates a stop command.

6. The system according to claim 1, wherein the instructions executable by the processor render the system further operative to, prior to returning to step [$S_{12}$], execute an updating process, comprising:
calculating an updated set of candidate beams (B') based on the updated treatment plan (x'), the updated set of candidate beams (B') being a subset of the set of candidate beams (B);
setting the updated set of candidate beams (B') to the set of candidate beams (B);
calculating an updated feasible region (X') reflecting the requirements of the feasible region (X) and a requirement that only beams in the set of candidate beams (B) can be used in the treatment plan (x); and
setting the updated feasible region (X') to the feasible region (X).

7. The system according to claim 6, wherein the instructions executable by the processor render the system further operative to:
following the updating process and prior to returning to step [$S_{12}$], calculate a further updated treatment plan (x") based on the updated treatment plan (x') and the feasible region (X), the feasible region (X) comprising the further updated treatment plan (x").

8. The system according to claim 7, wherein the updated set of candidate beams (B') is calculated such that an objective function value (F(x")) for the further updated treatment plan (x") is as close as possible to an objective function value (F(x')) for the updated treatment plan (x').

9. The system according to claim 6, wherein the instructions executable by the processor render the system further operative to, following the updating process and prior to returning to step [$S_{12}$], execute one of the steps:
setting the updated treatment plan (x') to the treatment plan (x); or
setting the further updated treatment plan (x") to the treatment plan (x).

10. The system according to claim 6, wherein the updated set of candidate beams (B') is calculated such that at least one of the following is satisfied prior to returning to step [$S_{12}$]:
[i] a first complexity measure ($\tau(x")$) of the further updated treatment plan (x") is less than or equal to the maximum first complexity ($\hat{\tau}$); and
[ii]: a second complexity measure (t(x")) of the further updated treatment plan (x") is less than or equal to the maximum second complexity ($\hat{t}$).

11. The system according to claim 6, wherein the instructions executable by the processor render the system further operative to:
calculate the updated set of candidate beams (B') by excluding at least one beam from the set of candidate beams (B), which excluded at least one beam contributes the least to the updated treatment plan (x').

12. The system according to claim 1, wherein at least one of the objective function (F) and the feasible region (X) describes a quality of a plan for the radiation therapy treatment in terms of a deviation of a planned dose (D) from a desired radiation dose ($D_{ref}$), the planned dose (D) being calculated on the basis of image data ($D_{img}$) defining the target volume.

13. The system according to claim 1, where the treatment plan (x) obtained in the set of inputs represents one of:
irradiating the target volume using a subset of the beams in the set of candidate beams (B), the therapeutic beam for each beam in the subset of the set of candidate beams (B) being conformed to the target volume and having a uniform fluence profile, the fluence profile for the therapeutic beam for each beam in the subset of the set of candidate beams (B) being scaled such that an average planned dose ($\overline{D}$) for the target volume is equal to a prescribed target dose;
delivering no irradiation; or
delivering irradiation using a subset of the beams in the set of candidate beams (B) according to a previously generated treatment plan.

14. The system according to claim 1, wherein the set of candidate beams (B) is a discretization of a continuous set of possible arrangements of the therapeutic beam, the continuous set of possible arrangements being based on at least one of:
a plurality of mechanical capabilities of a therapy machine,
a positioning of a patient relative to a therapy machine, and
a specification of desirable arrangements.

15. A method of planning a radiation therapy treatment in which a target volume is irradiated by a therapeutic beam, the method comprising the consecutive steps of:
[$S_{11}$] obtaining a set of inputs in a processor, the set of inputs comprising:
a set of candidate beams (B), each beam in the set of candidate beams (B) defining an arrangement of the therapeutic beam relative to the target volume;
a treatment plan (x) for the radiation therapy treatment that uses a subset of the candidate beams (B);
an objective function (F) describing a quality of the treatment plan (x); and
a feasible region (X) describing requirements on the treatment plan (x) that must be fulfilled,
at least one of the objective function (F) and the feasible region (X) reflecting a first complexity criterion ($\tau(x) \leq \hat{\tau}$), the first complexity criterion ($\tau(x) \leq \hat{\tau}$) limiting a first complexity measure ($\tau(x)$) to be less than or equal to a maximum first complexity ($\hat{\tau}$), the first complexity measure ($\tau(x)$) being related to a delivery time for the treatment plan (x);
[$S_{12}$] executing an optimization step whereby an updated treatment plan (x') is calculated by optimizing the treatment plan (x) with respect to the objective function (F) and the feasible region (X);
[$S_{13}$] checking if a termination criterion is fulfilled;
and if so, [$S_{131}$] calculating a set of selected beams (B*) based on the updated treatment plan (x'), the set of selected beams (B*) being a subset of the set of candidate beams (B);
and otherwise, [$S_{132}$] setting the updated treatment plan (x') to the treatment plan (x); calculating an updated first complexity criterion ($\tau'(x) \leq \hat{\tau}''$); setting the updated first complexity criterion ($\tau'(x) \leq \hat{\tau}'$) to the first complexity criterion ($\tau(x) \leq \hat{\tau}$); and returning to step [$S_{12}$],
wherein the first complexity criterion ($\tau(x) \leq \hat{\tau}$) represents a continuous and differentiable approximation of a second complexity criterion ($t(x) \leq \hat{t}$), the second complexity criterion ($t(x) \leq \hat{t}$) limiting a second complexity measure (t(x)) within a maximum second complexity ($\hat{t}$), the second complexity measure (t(x)) being indicative of a number of beams in the set of candidate beams (B) that is used in the treatment plan (x);

prior to returning to step [$S_{12}$], calculating an updated second complexity criterion (t'(x)≤t̂'); and setting the updated second complexity criterion (t'(x)≤t̂') to the second complexity criterion (t(x)≤t̂).

16. The method according to claim 15, comprising:
receiving definitions of the objective function (F) and the feasible region (X) via at least one input interface, and outputting the determined set of selected beams (B*) via an output interface.

17. The method according to claim 15, wherein the set of inputs further comprises a final maximum first complexity ($\tau_{max}$), and the method further comprises:
calculating the updated first complexity criterion (τ(x)≤τ̂') such that, prior to returning to a final iteration of step [$S_{12}$], the maximum first complexity (τ̂) is equal to the final maximum first complexity ($\tau_{max}$).

18. The method according to claim 15, wherein the set of inputs further comprises a final maximum second complexity ($t_{max}$), and the method further comprises:
calculating the updated second complexity criterion (t'(x)≤t̂') such that, prior to returning to a final iteration of step [$S_{12}$], the maximum second complexity (t̂) is equal to the final maximum second complexity ($t_{max}$).

19. The method according to claim 18, wherein the termination criterion is based on at least one of:
[a] a maximum number of iterations of step [$S_{12}$],
[b] the first complexity measure (τ(x)) is less than or equal to the final maximum first complexity ($\tau_{max}$),
[c] the second complexity measure (t(x)) is less than or equal to the final maximum second complexity ($t_{max}$), and
[d] a user input (S) is received, which user input (S) designates a stop command.

20. The method according to claim 19, further comprising:
calculating the updated set of candidate beams (B') by excluding at least one beam from the set of candidate beams (B), which excluded at least one beam contributes the least to the updated treatment plan (x').

21. The method according to claim 15, further comprising, prior to returning to step [$S_{12}$], executing an updating process involving:
calculating an updated set of candidate beams (B') based on the updated treatment plan (x'), the updated set of candidate beams (B') being a subset of the set of candidate beams (B);
setting the updated set of candidate beams (B') to the set of candidate beams (B); calculating an updated feasible region (X') reflecting the requirements of the feasible region (X) and a requirement that only beams in the set of candidate beams (B) can be used in the treatment plan (x); and
setting the updated feasible region (X') to the feasible region (X).

22. The method according to claim 21, further comprising:
following the updating process and prior to returning to step [$S_{12}$], calculating a further updated treatment plan (x") based on the updated treatment plan (x') and the feasible region (X), the feasible region (X) comprising the further updated treatment plan (x").

23. The method according to claim 21, further comprising, following the updating process and prior to returning to step [$S_{12}$], executing one of the steps:
setting the updated treatment plan (x') to the treatment plan (x); or
setting the further updated treatment plan (x") to the treatment plan (x).

24. The method according to claim 21, comprising calculating the updated set of candidate beams (B') such that at least one of the following is satisfied prior to returning to step [$S_{12}$]:
[i] a first complexity measure (τ(x")) of the further updated treatment plan (x") is less than or equal to the maximum first complexity (τ̂); and
[ii]: a second complexity measure (t(x")) of the further updated treatment plan (x") is less than or equal to the maximum second complexity (t̂).

25. The method according to claim 24, comprising:
calculating the updated set of candidate beams (B') such that an objective function value (F(x")) for the further updated treatment plan (x") is as close as possible to an objective function value (F(x')) for the updated treatment plan (x').

26. The method according to claim 15, wherein at least one of the objective function (F) and the feasible region (X) describes a quality of a plan for the radiation therapy treatment in terms of a deviation of a planned dose (D) from a desired radiation dose ($D_{ref}$), and the method comprises:
calculating the planned dose (D) on the basis of image data ($D_{img}$) defining the target volume.

27. The method according to claim 15, where the treatment plan (x) obtained in the set of inputs represents one of:
irradiating the target volume using a subset of the beams in the set of candidate beams (B), the therapeutic beam for each beam in the subset of the set of candidate beams (B) being conformed to the target volume and having a uniform fluence profile, the fluence profile for the therapeutic beam for each beam in the subset of the set of candidate beams (B) being scaled such that an average planned dose ($\overline{D}$) for the target volume is equal to a prescribed target dose;
delivering no irradiation; or
delivering irradiation using a subset of the beams in the set of candidate beams (B) according to a previously generated treatment plan.

28. The method according to claim 15, wherein the set of candidate beams (B) is a discretization of a continuous set of possible arrangements of the therapeutic beam, the continuous set of possible arrangements being based on at least one of:
a plurality of mechanical capabilities of a therapy machine,
a positioning of a patient relative to a therapy machine, and
a specification of desirable arrangements.

29. A non-volatile computer readable medium containing a computer program comprising instructions which, when executed on at least one processor, cause the at least one processor to carry out the method according to claim 15.

* * * * *